(12) United States Patent
Wu et al.

(10) Patent No.: US 9,689,008 B2
(45) Date of Patent: Jun. 27, 2017

(54) FERMENTATION METHOD FOR PRODUCING CO-ENZYME Q10

(75) Inventors: Yi Wu, Huhho (CN); Biqin Chen, Huhhot (CN); Guanghuang Zhan, Huhhot (CN); Youpao Zhu, Huhhot (CN)

(73) Assignees: Inner Mongolia Kingdomway Pharmaceutical Limited, Huhhot, Inner Mongolia (CN); Xiamen Kingdomway Group Company, Xiamen, Fujian (CN)

( * ) Notice: Subject to any disclaimer, the term of this patent is extended or adjusted under 35 U.S.C. 154(b) by 750 days.

(21) Appl. No.: 13/996,596

(22) PCT Filed: Aug. 10, 2011

(86) PCT No.: PCT/CN2011/078199
§ 371 (c)(1),
(2), (4) Date: Jul. 30, 2013

(87) PCT Pub. No.: WO2012/083702
PCT Pub. Date: Jun. 28, 2012

(65) Prior Publication Data
US 2013/0302862 A1 Nov. 14, 2013

(30) Foreign Application Priority Data
Dec. 23, 2010 (CN) .......................... 2010 1 0601223

(51) Int. Cl.
*C12P 7/66* (2006.01)
*C12N 1/38* (2006.01)

(52) U.S. Cl.
CPC . *C12P 7/66* (2013.01); *C12N 1/38* (2013.01)

(58) Field of Classification Search
None
See application file for complete search history.

(56) References Cited

U.S. PATENT DOCUMENTS 3,767,534 A * 10/1973 Miura ...................... C12N 1/00
435/243
4,013,731 A * 3/1977 Asahina ............... A61K 31/045
568/875
(Continued)

FOREIGN PATENT DOCUMENTS

CN 101333509 A 12/2008
CN 102154182 A 8/2011
(Continued)

OTHER PUBLICATIONS

Qiao Zhinxin, Rapid screening of strains with improved coenzyme Q10 production by genome shuffling (2009), w/ English Abstract.
(Continued)

*Primary Examiner* — Blaine Lankford
*Assistant Examiner* — Lauren K Van Buren
(74) *Attorney, Agent, or Firm* — RatnerPrestia

(57) ABSTRACT

A fermentation method for producing coenzyme Q10 is provided, including stepwisly culturing of microbial strains capable of producing coenzyme Q10, wherein key promoting factors are added in each stage of culture, and in the stage of culture in a fermentor, dissolved oxygen feedback-fed batch culture technique is adopted to realize the feedback regulation of the production of coenzyme Q10, so as to improve the yield of coenzyme Q10.

7 Claims, 2 Drawing Sheets

(56) References Cited

U.S. PATENT DOCUMENTS

| | | | | |
|---|---|---|---|---|
| 4,070,244 A | * | 1/1978 | Nakao | C12P 7/66 |
| | | | | 435/133 |
| 2005/0153406 A1 | * | 7/2005 | Murata | C12P 7/66 |
| | | | | 435/133 |
| 2008/0152707 A1 | * | 6/2008 | Fantuzzi | A23L 1/30 |
| | | | | 424/456 |
| 2009/0226986 A1 | * | 9/2009 | Berry | C12N 9/0006 |
| | | | | 435/133 |

FOREIGN PATENT DOCUMENTS

| WO | WO 2008/100782 A2 | | 8/2008 |
|---|---|---|---|
| WO | WO2008100782 | * | 8/2008 |
| WO | WO2008134766 | * | 11/2008 |

OTHER PUBLICATIONS

First Office Action issued for priority Chinese Application No. 201010601223.5 on Aug. 3, 2012, w/ English Translation.
Second Office Action issued for priority Chinese Application No. 201010601223.5 on May 3, 2013, w/ English Translation.
Wu et al., World Journal of Microbiology & Biotechnology, 19:925-28 (2003).
Li et al., Biotechnology Bulletin, 2:59-62 (2009).
Yen & Shih, Bioprocess Biosyst Eng, 32:711-16 (2009).
PCT/CN2011/078199 International Search Report by Zhenyu Yang mailed Nov. 24, 2011.

* cited by examiner

FERMENTATION METHOD FOR PRODUCING CO-ENZYME Q10

CROSS REFERENCE TO RELATED APPLICATIONS

This application is the U.S. National Phase Application of PCT/CN2011/078199, filed Aug. 10, 2011, which claims priority to Chinese Application No. 201010601223.5, filed Dec. 23, 2010, the contents of such applications being incorporated by reference herein.

TECHNICAL FIELD

The invention relates to the field of Fermentation Engineering, in particular, relates to a fermentation method for producing coenzyme Q10.

BACKGROUND ART

Coenzyme Q10, also called ubiquinone, is a lipid-soluble quinone compound, is a native anti-oxidant and a cellular metabolism activator produced by cells, is widely present in animals, plants and microorganisms, and is an important hydrogen carrier in respiratory chain of biological cells. Meanwhile, due to native oxidation-reduction property of quinone ring, coenzyme Q10 plays a role in protecting and recovering the integrity of biological membrane structure, stabilizing membrane potential, enhancing immune response, and the like. In recent years, coenzyme Q10, as a good biochemical agent, has been widely applied to various cardiopathys, diabetes, cancers, acute and chronic hepatitis, Parkinson's Disease, and the like, has been used to prevent arteriosclerosis, apoplexy and hypertension, and has a good health care effect on heart, liver and kidney. In addition, coenzyme Q10 also has an anti-aging effect, and thus is widely applied in the field of cosmetics and health products.

Recently, the production of coenzyme Q10 at home and abroad is mainly based on fermentation methods using microorganisms. Extraction methods from animal or plant tissues are restricted in large-scale production due to limited sources, high cost of raw materials, complicated chemical components, and low content of coenzyme Q10. Chemical synthesis methods are not suitable for modern industrial production due to stringent synthetic conditions, complex processes, products as mixtures of cis-isomers and trans-isomers, and low biological activity. Fermentation methods for producing coenzyme Q10 using microorganisms have advantages such as rich sources of raw materials, low cost, mild reaction conditions, and high biological activity of products, and thus become the most potential production methods.

Recently, the studies on fermentation methods for producing coenzyme Q10 using microorganisms are mainly focused on selection and culture of high-yield microbial strains and lab experiment level of fermentation. For example, in the patent application "*Rhodobacter sphaeroides* mutant of coenzyme Q10 and culturing method" as filed by "Tianchen Shenzhou Ind. Co Ltd.", a mutant strain is obtained by means of space mutagenesis, and the fermentation unit thereof reaches 0.8 g/L; Qiao Zhixin et al., obtained high-yield strains by rapid fusion of multiple forward mutations using genome shuffling in combination with traditional mutation breeding, wherein the yield of coenzyme Q10 per unit of thalli was 8.31 mg/g. In current, there are few studies on processes of producing coenzyme Q10 in industrial scale, the fermentation level is low generally, the cycle is long, and the cost is high. In addition to the obtainment of high-yield microbial strains by various mutagenesis techniques, the addition of key promoting factors during stepwise enlargement culture and the application of dissolved oxygen feedback-fed batch culture technique to fermentation are also effective ways to enhance productivity of coenzyme Q10. There are no relevant reports yet.

CONTENTS OF INVENTION

In order to further improve the yield of coenzyme Q10, the inventors carried out a large number of repeated experiments to optimize the culture methods and conditions in multiple aspects, thereby achieving a great increase in the yield of coenzyme Q10 and accomplishing the invention.

In the first aspect, the invention relates to a fermentation method for producing coenzyme Q10, which is stepwisly culturing of microbial strains capable of producing coenzyme Q10, characterized by:

a) adding key promoting factors in each stage of culture, wherein the key promoting factors are selected from the group consisting of one or more of vitamins, amino acids, steroids, solanesol, p-hydroxybenzoic acid, and beta-carotene; and/or b) in the stage of culturing in a fermentor, using dissolved-oxygen feedback and fed-batch technique, which includes starting to feed glucose when dissolved-oxygen value is sharply raised, and retaining a 5% dissolved-oxygen all the time during culture.

In the invention, the microbial strains capable of producing coenzyme Q10 comprise *Rhodopseudomonas palustris, Rhodopseudomonas capsulatus, Rhodopseudomonas gelatinosa, Pseudomonas aeruginosa, Pseudomonas denitrificans, Bullera pseudoalba, Candida tropicalis, Sporobolomyces roseus, Paracoccus denitrificans, Cryptococcus neoformans, Acetobacter, Agrobacterium tumefaciens, Protaminobacter, Rhizobus radiobacterium, Rhizobium leguminosarum, Rhodopseudomonas rubrum, Rhodobacter capsulatus, Rhodobacter sphaeroides, Rhodobacter sulfidophilus, Cryptococcus neoformans, Aspergillus fumigates, Ustilago zea*, and the like; preferably *Rhodobacter sphaeroides*. In an embodiment of the invention, the microbial strain capable of producing coenzyme Q10 is *Rhodobacter sphaeroides* JDW-610 mutant strain, wherein the mutant strain was deposited in China General Microbiological Culture Collection Center (CGMCC), with an deposition number of CGMCC No. 4497 and a deposition date of Dec. 21, 2010.

In the invention, stepwisly culturing is used, including culturing in a stock bottle, culturing in a seeding tank and culturing in a fermentor. The culturing in a seeding tank may be the culturing in a primary seeding tank, or the culturing in a primary seeding tank and a secondary seeding tank.

In the invention, the activation of microbial strains includes:

(1) passage of microbial strain: employing slant passage, wherein the medium is a broth medium, and culturing at 30° C. in dark for 4 days until grass green circular colonies with a diameter of about 1.4-2.0 mm appear;

(2) culture in a stock bottle the composition of medium: 10 g glucose, 6 g yeast extract, 5 g peptone, 5 g sodium chloride, 0.75 g ammonia sulfate, 1 g magnesium sulfate, 0.3 g monopotassium phosphate, 0.2 g ferrous sulfate, 0.05 g manganese sulfate, 0.03 g potassium nitrate, 0.007 g zinc sulfate, and 1000 ml water, with pH 7.2, sterilized at a temperature of 121° C. for 25 min, wherein the stock bottle was placed in a shaker at 30° C., 300 rpm for 25 h.

In the invention, the composition of the seed medium and the basic fermentation medium vary depending on the microbial strains selected.

In an embodiment of the invention, the composition of seed medium is: 3-10 g glucose, 1-5 g yeast powder, 2-6 g ammonia sulfate, 0.5-2 g aginomoto, 0.3-2 g corn steep liquor powder, 1-4 g magnesium sulfate, 0.3-2 g monopotassium phosphate, 1-4 g sodium chloride, 0.2-1 g ferrous sulfate, 0.03-0.1 g manganese sulfate, 0.001-0.01 g zinc sulfate, 5-10 g calcium carbonate, 1000 ml water, with pH 6.5-7.0.

In an embodiment of the invention, the composition of basic fermentation medium is: 10-20 g glucose, 3-10 g ammonia sulfate, 2-8 g aginomoto, 4-9 g corn steep liquor powder, 5-10 g magnesium sulfate, 0.1-0.5 g monopotassium phosphate, 1-5 g sodium chloride, 1-3 g ferrous sulfate, 0.1-0.4 g manganese sulfate, 0.005-0.01 g cobalt dichloride, 1000 ml water, with pH 6.5-7.0.

In the invention, the conditions for each stage of culture are selected depending on microbial strains, mediums, and charging volumes.

In an embodiment of the invention, the culture conditions for the primary seeding tank, the secondary seeding tank and the fermentor are:

the primary seeding tank: with agitation rate of 200-500 rpm, airflow rate of 0.5-2 vvm, temperature of 28-32° C., and pressure of 0.02-0.05 MPa for 20-50 h; and/or the secondary seeding tank: with agitation rate of 100-400 rpm, airflow rate of 0.3-1 vvm, temperature of 28-32° C., and pressure of 0.02-0.05 MPa for 10-30 h; and/or the fermentor: with agitation rate of 90-130 rpm, airflow rate of 0.3-1 vvm, temperature of 30-35° C., and pressure of 0.03-0.06 MPa for 70-100 h.

In the invention, key promoting factors are added in each stage of culture; among the key promoting factors, vitamins include, but are not limited to, oryzanin, lactoflavine, niacin, choline, pantothenic acid or calcium pantothenate, pyridoxines, biotin, folic acid, cyanocobalamin, inose and ascorbic acid; amino acids include, but are not limited to, tyrosine, methionine, tryptophan, histidine, glycine, serine, phenylalanine, methionine, valine, isoleucine and asparagines; steroids include, but are not limited to, ergosterol and cholic acid.

In an embodiment of the invention, the preferred combination of the key promoting factors is a combination of solanesol, beta-carotene, tyrosine, phenylalanine, ergosterol, oryzanin, lactoflavine, calcium pantothenate and niacin.

In the invention, the key promoting factors are added in each stage of culture in the following manners:

(1) being added to the medium prior to seeding, including a stock bottle, a seeding tank (which may be a primary seeding tank, or a primary and secondary seeding tank) and a fermentor; the added amounts of the key promoting factors being 0.006-0.04 g solanesol, 0.004-0.05 g tyrosine, 0.004-0.05 g beta-carotene, 0.004-0.045 g phenylalanine, 0.003-0.015 g ergosterol, 0.3-1.25 g oryzanin, 0.3-1.25 g lactoflavine, 0.02-0.25 g calcium pantothenate, and 0.2-1 g niacin, per liter of medium or fermentation liquor; and/or (2) being added by feeding nutrient-source materials at a variable rate in the exponential phase of culturing in the fermentor, wherein the composition of said nutrient-source materials is: basic fermentation medium concentrated to 3-times and key promoting factors; and the added amounts of said key promoting factors are 0.0005-0.0048 g solanesol, 0.0004-0.006 g tyrosine, 0.0004-0.006 g beta-carotene, 0.0004-0.0054 g phenylalanine, 0.0003-0.0018 g ergosterol, 0.027-0.15 g oryzanin, 0.027-0.15 g lactoflavine, 0.0018-0.03 g pantothenate calcium, 0.018-0.12 g niacin per one liter of fermentation liquor, calculated on the basis of the volume of the fermentation liquor before the addition; the volume of the nutrient-source materials is 3-10% of the volume of the fermentation liquor.

In step b) according to the first aspect of the invention, under the conditions of retaining 5% dissolved oxygen during culture, glucose consumption is accelerated by evenly increasing the agitation rate and airflow rate in the exponential phase of fermentation, so that the concentration of thalli reaches toe 80 g/L or higher at the end of exponential phase.

In the invention, the evenly increasing the agitation rate and airflow rate refers to the increase of agitation rate and airflow rate respectively to 100-130 rpm and 0.6-1 vvm, at a rate of 5-40 rpm and 0.1-0.6 vvm per 5-10 h from initial conditions.

The method according to the first aspect of the invention, further comprises feeding nutrient-source materials at a variable rate in the exponential phase of fermentation during culturing in the fermentor, the volume of the nutrient-source materials being 3-10% of the volume of the fermentation liquor, the composition of said nutrient-source materials being: basic fermentation medium concentrated to 3-times and the key promoting factors of the invention.

In the invention, said feeding of nutrient-source materials at a variable rate refers to the feeding of all the nutrient-source materials to the fermentor by the end of the exponential phase by setting the initial flow rate of feeding nutrient-source materials to be 1~3 L/h (as calculated on the basis of per $m^3$ fermentation liquor), with the flow rate being increased by 0.6~1.6 L/h per 5-10 h (as calculated on the basis of per $m^3$ fermentation liquor), depending on the length of the exponential phase of fermentation.

The method according to the first aspect of the invention, further comprises, in the stage of culturing in the fermentor of the invention, feeding potassium dihydrogen phosphate solution to control the dissolved phosphorus level in different stages: 0.14-0.18 g/L at the early stage of fermentation, 0.08-0.12 g/L at the mid-late stage of fermentation; meanwhile feeding ammonia to adjust the pH value of the fermentation liquor between 6.5-7.0, the nitrogen content of the amino group is controlled within 0.8-1.5 g/L.

The fermentation is stopped when the staining of the thalli turns pale, some hyphae are self-dissolved, and the titer increases slowly during culture in the fermentor.

In another aspect, the invention relates to a fermentation method for producing coenzyme Q10, comprising the following steps;

slant subculturing *Rhodobacter sphaeroides* JDW-610 mutant strain and culturing them in a stock bottle, followed by culturing them in a sterilized primary seeding tank with agitation rate of 200-500 rpm, airflow rate of 0.5-2 vvm, temperature of 28-32° C., and pressure of 0.02-0.05 MPa for 20-50 h;

when the thalli in the primary seeding liquor are in a homogeneous state and are rich in amount and the sterility is up to standard, transferring all of them into a sterilized secondary seeding tank and culturing them with agitation rate of 100-400 rpm, airflow rate of 0.3-1 vvm, temperature of 28-32° C., and pressure of 0.02-0.05 MPa for 10-30 h, wherein the composition of medium in the primary and secondary seeding tank is: 3-10 g glucose, 1-5 g yeast powder, 2-6 g ammonia sulfate, 0.5-2 g aginomoto, 0.3-2 g corn steep liquor powder, 1-4 g magnesium sulfate, 0.3-2 g monopotassium phosphate, 1-4 g sodium chloride, 0.2-1 g ferrous sulfate, 0.03-0.1 g manganese sulfate, 0.001-0.01 g zinc sulfate, 5-10 g calcium carbonate, and 1000 ml water, with pH 6.5-7.0; prior to seeding, transferring the sterilized key promoting factors into the medium in the stock bottle, the primary seeding tank and the secondary seeding tank, wherein the added amounts of the key promoting factors are 0.006-0.04 g solanesol, 0.004-0.05 g tyrosine, 0.004-0.05 g beta-carotene, 0.004-0.045 g phenylalanine, 0.003-0.015 g ergosterol, 0.3-1.25 g oryzanin, 0.3-1.25 g lactoflavine, 0.02-0.25 g calcium pantothenate and 0.2-1 g niacin, per liter of medium;

under sterile conditions, transferring the cultured secondary seeding liquor into a fermentor, wherein the composition of fermentation medium is: 10-20 g glucose, 3-10 g ammonia sulfate, 2-8 g aginomoto, 4-9 g corn steep liquor powder, 5-10 g magnesium sulfate, 0.1-0.5 g monopotassium phosphate, 1-5 g sodium chloride, ferrous sulfate 1-3 g, 0.1-0.4 g manganese sulfate, 0.005-0.01 g cobalt dichloride and 1000 ml water, with pH 6.5-7.0; prior to seeding, transferring the sterilized key promoting factors into the fermentation liquor in the fermentor, wherein the added amounts are the same as the amounts of the key promoting factors added to the stock bottle and the seeding tanks;

Culturing the fermentation liquor with agitation rate of 90-130 rpm, airflow rate of 0.3-1 vvm, temperature of 30-35° C., and pressure of 0.03-0.06 MPa for 70-100 h; when the dissolved oxygen value increases sharply, feeding glucose to retain 5% dissolved oxygen at the time during culture; accelerating glucose consumption by evenly increasing the agitation rate and airflow rate in the exponential phase of fermentation, so that the concentration of thalli reaches to 80 g/L or higher at the end of the exponential phase; meanwhile, feeding nutrient-source materials at a variable rate, wherein the volume of the nutrient-source materials is 3-10% of the volume of the fermentation liquor, and the added amounts of the key promoting factors are 0.0005-0.0048 g solanesol, 0.0004-0.006 g tyrosine, 0.0004-0.006 g beta-carotene, 0.0004-0.0054 g phenylalanine, 0.0003-0.0018 g ergosterol, 0.027-0.15 g oryzanin, 0.027-0.15 g lactoflavine, 0.0018-0.03 g calcium pantothenate, and 0.018-0.12 g niacin, per liter of fermentation liquor, calculated on the basis of the volume of the fermentation liquor before the addition; feeding monopotassium phosphate solution during fermentation to control the dissolved phosphor within 0.14-0.18 g/L and 0.08-0.12 g/L at early state and the mid-late stage of fermentation, respectively, feeding ammonia to adjust the pH value of the fermentation liquor between 6.5-7.0, controlling the nitrogen content of the amino group within 0.8-1.5 g/L; wherein the resultant mixture is discharged from the fermentor when the staining of thalli turns pale, some hyphae are self-dissolved, and the titer increases slowly.

In the invention, the culturing in a seeding tank refers to after culturing in the stock culture, a seed enlargment culture carried out in order to make the total amount and concentration of thalli meet the requirement of fermentor culturing, which may be a culture in a primary seeding tank, or may be a culture in a primary seeding tank and secondary seeding tank.

In the invention, the exponential phase of fermentation varies depending on microbial strains, mediums and culture conditions, and refers to a phase during which the concentration of thalli increases in a logarithmic manner to a stable level. In general, when the fermentation is carried out for 10-60 hours, the period when the concentration tends to be stable is the end of exponential phase.

In the invention, the early stage of fermentation varies depending on microbial strains, mediums and culture conditions, and refers to a stage from the initiation of fermentation to the end of exponential phase.

In the invention, the mid-late stage of fermentation varies depending on microbial strains, mediums and culture conditions, and refers to a stage from the phase of a stable concentration of thalli to the end of fermentation.

In the invention, the value shown in the dissolved oxygen meter decreases continuously as glucose is consumed in fermentation process, and the sharp increase of dissolved oxygen refers to such a process that the value shown in the dissolved oxygen meter rebounds from the lowest point to the relatively higher point in a short time when glucose is used up.

Advantageous Effects of the Invention

In the invention, key promoting factors are added during stepwisly culturing of coenzyme Q10, and meanwhile the dissolved oxygen feedback-fed batch culture technique is employed in the stage of culture in a fermentor, and the feedback regulation of coenzyme Q10 is accomplished by strategies such as feeding glucose depending on the dissolved oxygen feedback, feeding nutrient-source materials at a variable rate and continuously feeding phosphoric water and ammonia, thereby effectively increasing cell density. The preferred combinations of key promoting factors are obtained preferably depending on the biosynthetic pathway of coenzyme Q10 in combination with bacterial metabolic regulation mechanism. The addition of preferred combinations effectively promotes growth of thalli, obtains a high cell density, blocks or reduces branched metabolic pathway, enhances metabolic throughput of coenzyme Q10, and achieves the effect of increasing yield. In the stage of culture in a fermentor, the dissolved oxygen feedback-fed batch culture technique is employed to keep bacteria at an appropriate growth rate at the early stage of fermentation so as to obtain a high cell density, a certain dissolved oxygen value is maintained at the mid-late stage of fermentation to avoid conditions with a too low dissolved oxygen that accelerate the ageing of thalli, so as to fulfill the object of prolonging the accumulation time of products. Meanwhile, the control of glucose concentration at a low level effectively inhibits the production and accumulation of metabolic side-products. Due to the feedback regulation of coenzyme Q10 by strategies such as feeding glucose depending on the dissolved oxygen feedback, feeding nutrient-source materials at a variable rate and continuously feeding phosphoric water and ammonia, the metabolic flow is effectively controlled, the synthetic period of products is prolonged, and the yield of coenzyme Q10 reaches to 3400 mg/L or higher, which is greatly increased as compared to original fermentation level. The process of the invention is stable and the fermentation cost is greatly reduced.

SPECIFIC MODE FOR CARRYING OUT THE INVENTION

Figure 1:
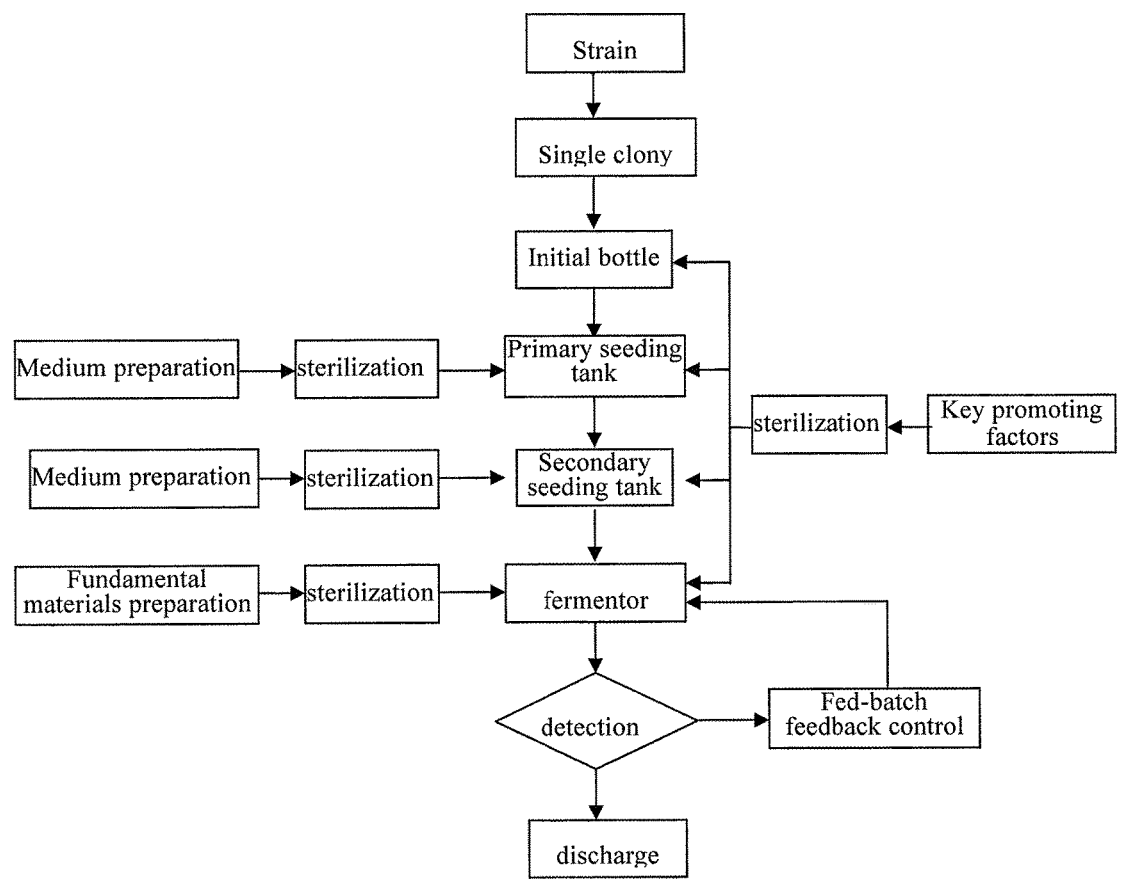
FIG. 1 illustrates a flow chart for the fermentation process of the invention.

The embodiments of the invention are described in detail by combining the following examples. However, a person skilled in the art would understand that the following examples are only used to illustrate the invention rather than defining the scope of the invention. When no particular conditions are specified in the examples, the examples are carried out under conventional conditions or the conditions recommended by the manufacturer. The agents or instruments, whose manufacturers are not indicated, are conventional products that are available commercially.

Example 1

The Method for Determining the Content of Coenzyme Q10 in a Fermentation Liquor The content of coenzyme Q10 in a fermentation liquor is determined by the method for determining coenzyme Q10 as described in Pharmacopoeia of People's Republic of China (the second edition, 2010).

In dark condition, 5 ml fermentation liquid cultures was drawn accurately and placed in a 50 ml volumetric flask. A drop of 6 mol/L HCl solution (about 0.1 ml), acetone (10 ml), 30% hydrogen peroxide (0.5 ml) were added, respectively, and the volumetric flask was slightly shaken. 30 ml absolute alcohol was added. The volumetric flask was subjected to ultrasound in an ultrasonic device for 30 s, and then the volumetric flask was taken out and absolute alcohol was added to the scale. The volumetric flask was subjected to ultrasonic extraction in an ultrasonic device for 45 min (the water temperature was controlled between 30° C. and 35° C.), and then was taken out and shaken up. The resultant solution was filtered through a disposable organic filter head (0.45 μm), the primary filtrate was discarded, the subsequent filtrate was collected and was subjected to High Performance Liquid Chromatography (HPLC) to determine the content of coenzyme Q10 in the fermentation liquor.

HPLC Conditions
chromatographic column: Hypersil ODS 4.6 mm×150 mm, 5 μm, a stainless steel column;
Detection wavelength: 275 nm;
Mobile phase: absolute alcohol: absolute methanol=35:65;
Flow rate: 1.1 ml/min;
Column temperature: 35° C.

Example 2

The *Rhodobacter sphaeroides* JDW-610 mutant strain was cultured in a plate at 30° C. for 4 days, grass green circular colony that grew well were picked out and put into a sterilized medium in an stock bottle, and then were cultured at 30° C., 300 rpm in a shaker for 25 h; the liquid cultures in the stock bottler was transferred into a sterilized primary seeding tank (charged with a volume of 0.7 m$^3$), and cultured with agitation rate of 400 rpm, airflow rate of 1 vvm, temperature of 30° C., and pressure of 0.04 MPa for 38 h. When the thalli in the primary seeding liquor were in a homogeneous state and were rich in amount and the sterility was up to standard, all the liquor was transferred into a sterilized secondary seeding tank (charged with a volume of 7 m$^3$) and was cultured with agitation rate of 200 rpm, airflow rate of 0.8 vvm, temperature of 30° C., and pressure of 0.04 MPa for 12 h. The composition of medium in the primary and secondary seeding tank is: 5 g glucose, 3 g yeast powder, 4 g ammonia sulfate, 1 g aginomoto, 0.8 g corn steep liquor powder, 2 g magnesium sulfate, 1 g monopotassium phosphate, 2.4 g sodium chloride, 0.5 g ferrous sulfate, 0.1 g manganese sulfate, 0.005 g zinc sulfate, 5 g calcium carbonate, and 1000 ml water, with pH 6.5, sterilized at 121° C. for 25 min. Prior to seeding, the sterilized key promoting factors were transferred into the medium in the stock bottle, the primary seeding tank and the secondary seeding tank, wherein the added amounts of the key promoting factors were 0.016 g solanesol, 0.012 g tyrosine, 0.012 g beta-carotene, 0.02 g phenylalanine, 0.006 g ergosterol, 0.6 g oryzanin, 0.6 g lactoflavine, 0.04 g calcium pantothenate, 0.4 g niacin per liter of medium.

When the thalli in the secondary seeding liquor were in a homogeneous state and were rich in amount and the sterility was up to standard, all the liquor was transferred into a 120 m$^3$ fermentor (charged with a volume of 50 m$^3$). The composition of basic fermentation medium is: 20 g glucose, 5 g ammonia sulfate, 5 g aginomoto, 7 g corn steep liquor powder, 7 g magnesium sulfate, 0.3 g monopotassium phosphate, 3 g sodium chloride, 2 g ferrous sulfate, 0.4 g manganese sulfate, 0.008 g cobalt dichloride, and 1000 ml water, with pH 6.5, sterilized at 121° C. for 25 min. Prior to seeding, the sterilized key promoting factors were transferred into the fermentation liquor in the fermentor, wherein the added amounts were the same as the amounts of the key promoting factors added to the stock bottle and the seeding tanks.

The fermentation liquor were cultured with agitation rate of 90 rpm, airflow rate of 0.4 vvm, temperature of 32° C., and pressure of 0.04 MPa for 88 h. During fermentation, when the dissolved oxygen value increased sharply, glucose was fed to retain 5% dissolved oxygen all the time during culture. When the fermentation was carried out for 30-60 h, glucose consumption was accelerated by evenly increasing the agitation rate and airflow rate respectively to 120 rpm and 1 vvm at a rate of 10 rpm and 0.2 vvm per 10 h, so that the concentration of thalli reaches to 80 g/L or higher by 60 h of fermentation. Meanwhile, 4.5 m$^3$ nutrient-source materials were fed at a variable rate wherein the initial flow rate was 100 L/h and was increased by 50 L/h per 10 h. The composition of nutrient-source materials is: basic fermentation medium concentrated to 3-times and key promoting factors; and the added amounts of the key promoting factors were 0.0022 g solanesol, 0.0016 g tyrosine, 0.0016 g beta-carotene, 0.0027 g phenylalanine, 0.0008 g ergosterol, 0.081 g oryzanin, 0.081 g lactoflavine, 0.0054 g calcium pantothenate, 0.054 g niacin, per liter of fermentation liquor, calculated on the basis of the volume of the fermentation liquor before the addition. The agitation rate, the airflow rate, the dissolved oxygen and pH value were determined and controlled online, residual glucose concentration, dissolved phosphor, nitrogen content of the amino group were determined offline, and the morphology of thalli was observed.

Monopotassium phosphate solution was fed during fermentation, the dissolved phosphor was controlled within 0.14-0.18 g/L from start to 60 h and was controlled within 0.08-0.12 g/L after 60 h, ammonia was added to adjust the pH value of the fermentation liquor between 6.5-7.0, and to control the nitrogen content of the amino group within 0.8-1.5 g/L. The resultant mixture was discharged from the fermentor when the staining of thalli turned pale, some hyphae were self-dissolved, and the titer increased slowly. Please see FIG. 1 for the flow chart of the fermentation process.

The fermentation liquor was treated by the method described in Example 1, and the content of coenzyme Q10 was determined by HPLC.

Meanwhile, a control was set, a fed-batch culture technology, wherein glucose concentration was used as feedback index, was used. Glucose was fed in the stage of culturing in a fermentor, the concentration of the residual glucose in the fermentation liquor was controlled within 10~20 g/L, the other processes were the same as those described in the Example.

In current, glucose feeding processes for producing coenzyme Q10 generally use a fed-batch culture technology wherein glucose concentration is used as feedback index. Namely, glucose is added in the stage of culture in a fermentor, and the concentration of the residual glucose in the fermentation liquor is controlled within a given range. In the control experiment, the concentration of the residual glucose was controlled within 10~20 g/L. The invention employed the dissolved-oxygen and fed-batch technique, wherein glucose was fed by using sharply raised dissolved-oxygen value as marker, and a 5% dissolved-oxygen was retained all the time during culture. In the exponential phase of fermentation, glucose consumption was accelerated by evenly increasing the agitation rate and airflow rate respectively to 100-130 rpm and 0.6-1 vvm at a rate of 5-40 rpm and 0.1-0.6 vvm per 5-10 h at initial conditions, so that the concentration of thalli reaches to 80 g/L or higher at the end of exponential phase. The experimental results are shown in Table 1.

TABLE 1

The effect of different glucose feeding processes on coenzyme Q10 fermentation

| Glucose feeding process | Fermentation time (hours) | dry cell weight at the 60$^{th}$ hours(g/L) | Coenzyme Q10 yield (mg/L) | The main byproduct content in the fermentation liquor (%) |
|---|---|---|---|---|
| Dissolved oxygen feedback-fed batch culture | 88 | 83 | 3417 | 2.1 |
| Fed-batch culture using glucose concentration as feedback index | 76 | 61 | 2569 | 7.8 |

It can be seen from Table 1 that the dissolved oxygen feedback culture technology used in the invention has the following advantages as compared to general glucose feeding technology:

(1) bacteria were kept at an appropriate growth rate at the early stage of fermentation so as to obtain a high cell density, and the dry cell weight reached 83 g/L at 60 h;

(2) a certain dissolved oxygen value was maintained at the mid-late stage of fermentation to avoid conditions with a too low dissolved oxygen that accelerate the aging of thalli; the fermentation cycle was 88 h, while the fermentation cycle of a general glucose feeding technology was 76 h, namely fulfilling the object of prolonging the accumulation time of products;

(3) the control of glucose concentration at a low level effectively inhibited the production and accumulation of metabolic byproducts, wherein the coenzyme Q10 yield reached 3417 mg/L, which was increased by 33% as compared to a general glucose feeding process, the content of the main byproduct in the fermentation liquor was 2.1% which was significantly lower than a general glucose feeding process.

Example 3

The *Rhodobacter sphaeroides* JDW-610 mutant strain was cultured in a plate at 30° C. for 4 days, green circular single colony that grew well were picked out and put into a sterilized medium in a stock bottle, and were cultured at 30° C., 300 rpm in a shaker for 25 h; the liquor cultures in the stock bottle was transferred into a sterilized seeding tank (charged with a volume of 7 L) and were cultured with agitation rate of 300 rpm, airflow rate of 0.8 vvm, temperature of 30° C. and pressure of 0.04 MPa for 20 h. The composition of medium in the seeding tank is: 5 g glucose, 3 g yeast powder, 4 g ammonia sulfate, 1 g aginomoto, 0.8 g corn steep liquor powder, 2 g magnesium sulfate, 1 g monopotassium phosphate, 2.4 g sodium chloride, 0.5 g ferrous sulfate, 0.1 g manganese sulfate, 0.005 g zinc sulfate, 5 g calcium carbonate, 1000 ml water, with pH 6.5, sterilized at 121° C. for 25 min. Prior to seeding, the sterilized key promoting factors were transferred into the medium in the stock bottle and the seeding tank, wherein the added amounts of the key promoting factors were 0.012 g solanesol, 0.015 g tyrosine, 0.01 g beta-carotene, 0.025 g phenylalanine, 0.008 g ergosterol, 0.3 g oryzanin, 0.3 g lactoflavine, 0.05 g calcium pantothenate, and 0.2 g niacin, per liter of medium.

When the thalli in the seeding liquor were in a homogeneous state, rich in amount and the sterility was up to standard, all the liquor was transferred into a 100 L fermentor (charged with a volume of 50 L). The composition of basic fermentation medium is: 20 g glucose, 5 g ammonia sulfate, 5 g aginomoto, 7 g corn steep liquor powder, 7 g magnesium sulfate, 0.3 g monopotassium phosphate, 3 g sodium chloride, 2 g ferrous sulfate, 0.4 g manganese sulfate, 0.008 g cobalt dichloride, and 1000 ml water, with pH 6.5, sterilized at 121° C. for 25 min. Prior to seeding, the sterilized key promoting factors were transferred into the fermentation liquor in the fermentor, wherein the added amounts were the same as the amounts of the key promoting factors added to the stock bottle and the seeding tanks.

The fermentation liquor was cultured with agitation rate of 100 rpm, airflow rate of 0.6 vvm, temperature of 32° C., and pressure of 0.04 MPa for 88 hours. During fermentation, when the dissolved oxygen value increased sharply, glucose was fed to retain 5% dissolved oxygen all the time during culture. When the fermentation was carried out for 30-60 hours, glucose consumption was accelerated by evenly increasing the agitation rate and airflow rate respectively to 130 rpm and 0.9 vvm at a rate of 10 rpm and 0.1 vvm per 10 h, so that the concentration of thalli reaches to 80 g/L or higher by 60 h of fermentation. Meanwhile, 4.5 L nutrient-source materials were fed at a variable rate wherein the initial flow rate was 100 mL/h and was increased by 50 mL/h per 10 h. The composition of nutrient-source materials is: basic fermentation medium concentrated to 3-times and key promoting factors; and the added amounts of the key promoting factors were 0.0025 g solanesol, 0.002 g tyrosine, 0.002 g beta-carotene, 0.003 g phenylalanine, 0.001 g ergosterol, 0.09 g oryzanin, 0.09 g lactoflavine, 0.006 g calcium pantothenate, and 0.06 g niacin per liter of fermentation liquor, calculated on the basis of the volume of the fermentation liquor before the addition. The agitation rate, the airflow rate, the dissolved oxygen and pH value were determined and controlled online, residual glucose concentration, dissolved phosphor, nitrogen content of amino group were determined offline, and the morphology of thalli was observed.

Monopotassium phosphate solution was fed during fermentation, the dissolved phosphor was controlled within 0.14-0.18 g/L from start to 60 h and was controlled within 0.08-0.12 g/L after 60 h, ammonia was added to adjust the pH value of the fermentation liquor between 6.5-7.0, and to control the nitrogen content of the amino group within 0.8-1.5 g/L. The resultant mixture was discharged from the fermentor when the staining of thalli turned pale, some hyphae were self-dissolved, and the titer increased slowly.

The fermentation liquor was treated by the method described in Example 1, and the content of coenzyme Q10 was determined by HPLC.

Figure 2:
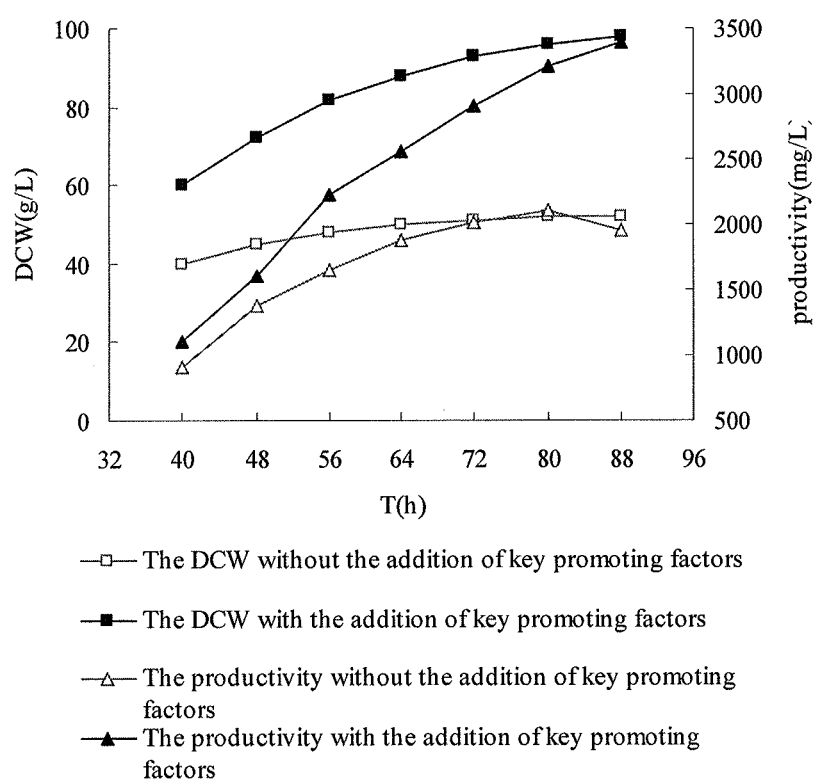
FIG. 2 illustrates the effect of the addition of key promoting factors on coenzyme Q10 fermentation; wherein the horizontal ordinate represents the fermentation time in a fermentor, and the unit is hour; the longitudinal coordinate DCW represents dry cell weight, the productivity refers to the yield of coenzyme Q10; the solid curve represents the results after the addition of key promoting factors.

Meanwhile, the control without the addition of key promoting factors was set, and the other processes were the same as those described in the Example. The experimental results are shown in FIG. 2.

It can be seen from FIG. 2 that the addition of key promoting factors in each stage of culture has a great effect on coenzyme Q10 fermentation, which is mainly shown in the following aspects.

(1) Vitamin additives such as oryzanin, lactoflavine, calcium pantothenate and niacin could effectively accelerate glycolysis rate and activate pentose-phosphate pathway, so as to promote the growth of thalli. The dry cell weight was 98 g/L at 88 h, which was significantly increased compared to the dry cell weight without addition of vitamin additives. Moreover, without the addition of vitamin additives, thalli were serious elongated and deformed, got aged easily, the titer increased slowly at the mid-late stage, and the period for secreting products was significantly shortened.

(2) Tyrosine, phenylalanine, ergosterol, beta-caroten and solanesol and the like effectively blocked or reduced branched metabolic pathway, relieved feedback inhibition, and enhanced metabolic throughput of coenzyme Q10. As the nutrient-source materials were fed, the titer of coenzyme Q10 increased quickly, and reached above 3400 mg/L at 88 h, while the titer was 1875 mg/L without the addition of them. Namely, the fermentation level was significantly increased.

Although the embodiments of the invention are described in detail, a person skilled in the art would understand that various modification and substitutions may be made to these details on the basis of all the teachings disclosed. These changes fall into the protection scope of the invention. The scope of the invention is defined by the attached claims and an equivalent thereof.

The invention claimed is:

1. A fermentation method for producing coenzyme Q10 comprising, culturing the strain, *Rhodobacter Sphaeroides* JDW-610, deposition number CGMCC No. 4497, by the following chronological stages: (1) culturing in a stock bottle, (2) culturing in a seeding tank, and (3) culturing in a fermentor, adding key promoting factors in each stage of culture, wherein the key promoting factors comprise solanesol, beta-carotene, tyrosine, phenylalanine, ergosterol, oryzanin, lactoflavin, calcium pantothenate, and niacin.

2. The fermentation method of claim 1, wherein the key promoting factors are added in the following manner:
(a) the key promoting factors are added to the medium prior to seeding the microbial strain in the stock bottle, the seeding tank, and the fermentor, the added amounts of key promoting factors being 0.006-0.04 g/L solanesol, 0.004-0.05 g/L tyrosine, 0.004-0.05 g/L beta-carotene, 0.004-0.045 g/L phenylalanine, 0.003-0.015 g/L ergosterol, 0.3-1.25 g/L oryzanin, 0.3-1.25 g/L lactoflavin, 0.02-0.25 g/L calcium pantothenate, 0.2-1 g/L niacin; and/or
(b) the key promoting factors are added at a variable rate during an exponential phase of fermentation of the microbial strain, wherein the added amounts of key promoting factors are 0.0005-0.0048 g/L solanesol, 0.0004-0.006 g/L tyrosine, 0.0004-0.006 g/L beta-carotene, 0.0004-0.0054 g/L phenylalanine, 0.0003-0.0018 g/L ergosterol, 0.027-0.15 g/L oryzanin, 0.027-0.15 g/L lactoflavin, 0.0018-0.03 g/L pantothenate calcium, 0.018-0.12 g/L niacin.

3. The fermentation method of claim 1, further comprising increasing evenly an agitation rate and an airflow rate to accelerate glucose consumption in an exponential phase of fermentation of the microbial strain.

4. The fermentation method of claim 3, wherein said agitation rate is increased evenly to 100-130 rpm from an initial agitation rate at a rate of 5-40 rpm per 5-10 h, and wherein said airflow rate is increased evenly to 0.6-1 vvm from an initial airflow rate at a rate of 0.1-0.6 vvm per 5-10 h.

5. The fermentation method of claim 1, wherein for each $m^3$ of fermentation liquid in the fermentor, said key promoting factors are added at a rate increased from an initial flow rate of 1-3 L/h by increasing 0.6-1.6 L/h per 5-10 h, and wherein the addition of said key promoting factors is completed by the end of the exponential phase.

6. The fermentation method of claim 1, wherein culturing in a fermentor further comprises feeding potassium di hydrogen phosphate solution to a fermentation liquor in the fermentor, whereby the fermentation liquor has dissolved phosphorus levels at 0.14-0.18 g/L at an early stage of fermentation of the microbial strain and 0.08-0.12 g/L at a mid-late stage of the fermentation; and feeding ammonia to the fermentation liquor, whereby the fermentation liquor has a pH value between 6.5-7.0 and a nitrogen content of 0.8-1.5 g/L.

7. The fermentation method of claim 1, wherein dissolved oxygen feedback feeds glucose into the fermentor when a sharp rise of dissolved oxygen is detected so as to maintain a 5% dissolved oxygen level.

* * * * *